United States Patent
Kitoh

(10) Patent No.: US 10,197,503 B2
(45) Date of Patent: Feb. 5, 2019

(54) FILM INSPECTION DEVICE

(71) Applicant: TOYOTA JIDOSHA KABUSHIKI KAISHA, Toyota-shi, Aichi-ken (JP)

(72) Inventor: Hiroki Kitoh, Tokai (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 0 days.

(21) Appl. No.: 15/698,862

(22) Filed: Sep. 8, 2017

(65) Prior Publication Data
US 2018/0100809 A1    Apr. 12, 2018

(30) Foreign Application Priority Data
Oct. 6, 2016 (JP) ................... 2016-198190

(51) Int. Cl.
| | | |
|---|---|---|
| G01N 21/89 | (2006.01) | |
| B65H 20/02 | (2006.01) | |
| G01N 21/896 | (2006.01) | |
| B65H 16/02 | (2006.01) | |

(52) U.S. Cl.
CPC ....... *G01N 21/8914* (2013.01); *B65H 16/026* (2013.01); *B65H 20/02* (2013.01); *G01N 21/896* (2013.01); *B65H 2801/72* (2013.01)

(58) Field of Classification Search
CPC ............. G01N 21/8914; G01N 21/896; B65H 16/026; B65H 20/02; B65H 2801/72
USPC ........................................................ 429/312
See application file for complete search history.

(56) References Cited

U.S. PATENT DOCUMENTS

| | | | | |
|---|---|---|---|---|
| 2014/0017579 A1* | 1/2014 | Hata | ............... | H01M 8/1253 |
| | | | | 429/408 |
| 2016/0093908 A1 | 3/2016 | Kitoh et al. | | |

FOREIGN PATENT DOCUMENTS

| | | |
|---|---|---|
| JP | 2013-4393 | 1/2013 |
| JP | 2014-229433 | 12/2014 |
| JP | 2015-207440 | 11/2015 |

* cited by examiner

*Primary Examiner* — Gary D Harris
(74) *Attorney, Agent, or Firm* — Finnegan, Henderson, Farabow, Garrett & Dunner, LLP

(57) ABSTRACT

A film inspection device is equipped with a first fixed roll, a second fixed roll, a first moving roll, and a second moving roll. The first and second fixed rolls stretch an electrolyte film, which includes a part that is irradiated with light between first and second driving rolls, from one surface side thereof. The first moving roll stretches the electrolyte film from the other surface side thereof. The second moving roll stretches the electrolyte film from the other surface side thereof. The second moving roll is moved such that a conveyance path of the electrolyte film between the second driving roll and the second fixed roll becomes short, while the first moving roll is moved such that the conveyance path of the electrolyte film between the first driving roll and the first fixed roll becomes long.

3 Claims, 6 Drawing Sheets

FILM INSPECTION DEVICE

INCORPORATION BY REFERENCE

The disclosure of Japanese Patent Application No. 2016-198190 filed on Oct. 6, 2016 including the specification, drawings and abstract is incorporated herein by reference in its entirety.

BACKGROUND

1. Technical Field

The present disclosure relates to a film inspection device.

2. Description of Related Art

As an electrolyte film used for a polymer electrolyte fuel cell, a reinforced electrolyte film including a porous reinforcing member therein is known. In Japanese Patent Application Publication No. 2014-229433 (JP 2014-229433 A), a process of manufacturing a reinforced electrolyte film is described. In concrete terms, it is described that a first band-shaped reinforcing member that is supported by a back sheet is arranged on a surface of a band-shaped electrolyte polymer that is supported by a back sheet, that a unilaterally reinforced film is formed by thermally press-fitting the band-shaped electrolyte polymer and the first band-shaped reinforcing member to each other by a hot roller, and that the back sheet on the band-shaped electrolyte polymer side is then peeled off from the unilaterally reinforced film. Besides, it is described that a second band-shaped reinforcing member that is supported by a back sheet is arranged on a surface of the unilaterally reinforced film from which the back sheet on the band-shaped electrolyte polymer side has been peeled off, that a bilaterally reinforced film is formed by thermally press-fitting the unilaterally reinforced film and the second band-shaped reinforcing member to each other by the hot roller, and that the back sheet on the first band-shaped reinforcing member side is then peeled off from the bilaterally reinforced film. Furthermore, it is described that the reinforced electrolyte film is formed by subjecting the bilaterally reinforced film, from which the back sheet on the first band-shaped reinforcing member side has been peeled off, to a hydrolysis treatment.

SUMMARY

In the process of manufacturing the reinforced electrolyte film, the film (the electrolyte film) is inspected as appropriate. For example, in the process of manufacturing the reinforced electrolyte film described in Japanese Patent Application Publication No. 2014-229433 (JP 2014-229433 A), the film is inspected after the bilaterally reinforced film is formed or after the reinforced electrolyte film is formed.

FIG. 6 is a schematic view showing the general configuration of an existing film inspection device 101 for inspecting an electrolyte film. As shown in FIG. 6, the film inspection device 101 is equipped with a first driving roll 102, a second driving roll 103, a light source 104, and a camera 105. The first driving roll 102 and the second driving roll 103 stretch an electrolyte film M as an object for inspection. The light source 104 irradiates a part of the electrolyte film M located between the first driving roll 102 and the second driving roll 103 with a light L1. The camera 105 faces the light source 104 across the electrolyte film M.

In inspecting the electrolyte film M, the electrolyte film M is conveyed in a forward direction S1 from the first driving roll 102 toward the second driving roll 103, by driving the first driving roll 102 and the second driving roll 103. When the electrolyte film M is conveyed in the forward direction S1, one surface side of the electrolyte film M is irradiated with the light L1 from the light source 104, and a light L2 leaking from the other surface side of the electrolyte film M is photographed by the camera 105. Then, image data photographed by the camera 105 are analyzed, and a defect present in the electrolyte film M is detected.

Before the inspection of the electrolyte film M is started, a processing of acquiring image data as a reference for determining a correction value of a shading correction needs to be performed first. In concrete terms, this processing is designed to irradiate the electrolyte film M with the light L1 by the light source 104 and acquire the image data by the camera 105, while conveying the electrolyte film M in the forward direction S1 by a predetermined distance d101 by positively rotating the first driving roll 102 and the second driving roll 103 (rotating the first driving roll 102 and the second driving roll 103 in a direction indicated by arrows R1 in the drawing). That is, the part of the electrolyte film M irradiated with the light L1 moves from a position A101 to a position A102 as shown in FIG. 6, and the image data on a region of the electrolyte film M located between the position A01 and the position A102 are acquired by the camera 105.

Then, after the image data as the reference for determining the correction value of the shading correction are acquired, the electrolyte film M is conveyed by the predetermined distance d101 in a backward direction S2 from the second driving roll 103 toward the first driving roll 102 by reversely rotating the first driving roll 102 and the second driving roll 103 (rotating the first driving roll 102 and the second driving roll 103 in a direction indicated by arrows R2 in the drawing). In this manner, the part of the electrolyte film M irradiated with light returns from the position A102 to the position A101.

After the processing of acquiring the image data as the reference for determining the correction value of the shading correction is completed, the electrolyte film M is inspected while conveying the electrolyte film M in the forward direction S1 by positively rotating the first driving roll 102 and the second driving roll 103.

By the way, as described above, a process of forming the bilaterally reinforced film in Japanese Patent Application Publication No. 2014-229433 (JP 2014-229433 A) includes a treatment of peeling off the base sheet from the electrolyte film. In the process including the treatment of peeling off the base sheet from the electrolyte film, the electrolyte film cannot be conveyed in the backward direction. This is because of the following reason. When the electrolyte film is conveyed in the backward direction, the base sheet that has been peeled off from the electrolyte film is stuck again on the electrolyte film. However, this may lead to an inconvenience in the electrolyte film.

As described above, with the existing film inspection device 101, in the processing of acquiring the image data as the reference for determining the correction value of the shading correction, the electrolyte film M is conveyed in the backward direction S2 to return a position of the electrolyte film M irradiated with the light L1. However, in the case where a process in which the electrolyte film cannot be conveyed in the backward direction, for example, the process including the treatment of peeling off the base sheet from the aforementioned electrolyte film is performed at a position upstream or downstream of a process of inspecting the film in the forward direction, it may be impossible to convey the electrolyte film in the backward direction in the processing of acquiring the image data as the reference for determining the correction value of the shading correction. Therefore, the film cannot be inspected as to the region of the electrolyte film M whose image data as the reference for determining the correction value of the shading correction are acquired (the region of the electrolyte film M located between the position A101 and the position A102), so that this region has to be discarded.

The present disclosure provides a film inspection device capable of inspecting a region of an electrolyte film whose image data as a reference for determining a correction value of a shading correction are acquired, even in the case where a process in which the electrolyte film cannot be conveyed in a backward direction is performed at a position upstream or downstream of a process of inspecting the film in a forward direction.

In an aspect of the present disclosure, a film inspection device is equipped with a first driving roll, a second driving roll, a light source, a camera, a first fixed roll, a second fixed roll, a first moving roll, and a second moving roll. The first driving roll stretches an electrolyte film as an object for inspection from one surface side thereof. The second driving roll stretches the electrolyte film as the object for inspection from one surface side thereof. The light source irradiates a part of the electrolyte film located between the first driving roll and the second driving roll with light. The camera is arranged facing the light source across the electrolyte film, and photographs light leaking from the electrolyte film. The first fixed roll stretches the electrolyte film from one surface side thereof between a part of the electrolyte film irradiated with light and the first driving roll. The second fixed roll stretches the electrolyte film from one surface side thereof between the part of the electrolyte film irradiated with light and the second driving roll. The first moving roll stretches the electrolyte film from the other surface side thereof between the first driving roll and the first fixed roll, and is movably configured. The second moving roll stretches the electrolyte film from the other surface side thereof between the second driving roll and the second fixed roll, and is movably configured. The second moving roll is moved such that a conveyance path of the electrolyte film between the second driving roll and the second fixed roll becomes short, while the first moving roll is moved such that the conveyance path of the electrolyte film between the first driving roll and the first fixed roll becomes long with the first driving roll and the second driving roll stopped, in a case where a region of the electrolyte film located between the first fixed roll and the second fixed roll is moved in a backward direction, which is an opposite of a forward direction from the first driving roll toward the second driving roll, in a processing of acquiring image data as a reference for determining a correction value of a shading correction. The electrolyte film is inspected while being conveyed in the forward direction. In the processing of acquiring the image data as the reference for determining the correction value of the shading correction, in the case where the region of the electrolyte film located between the first fixed roll and the second fixed roll is moved in the backward direction, the second moving roll is moved such that the conveyance path of the electrolyte film between the second driving roll and the second fixed roll becomes short, while the first moving roll is moved such that the conveyance path of the electrolyte film between the first driving roll and the first fixed roll becomes long, with the first driving roll and the second driving roll stopped. By moving the first moving roll and the second moving roll in this manner, the part of the electrolyte film located between the first fixed roll and the second fixed roll can be moved in the backward direction without driving the first driving roll and the second driving roll. When the part of the electrolyte film located between the first fixed roll and the second fixed roll is moved in the backward direction, the region of the electrolyte film whose image data as the reference for determining the correction value of the shading correction are acquired is located upstream of the part of the electrolyte film irradiated with light, in the forward direction. The electrolyte film is inspected while being moved in the forward direction, after the processing of acquiring the image data as the reference for determining the correction value of the shading correction. The region of the electrolyte film whose image data as the reference for determining the correction value of the shading correction are acquired is located upstream of the part of the electrolyte film irradiated with light, in the forward direction. Therefore, the electrolyte film M can also be inspected as to this region. Thus, even in the case where the process in which the electrolyte film cannot be conveyed in the backward direction is performed at a position upstream or downstream of the process of inspecting the film in the forward direction, the region of the electrolyte film whose image data as the reference for determining the correction value of the shading correction are acquired can be inspected.

Furthermore, the image data as the reference for determining the correction value of the shading correction may be acquired when the region of the electrolyte film located between the first fixed roll and the second fixed roll is moved in the backward direction by moving the second moving roll such that the conveyance path of the electrolyte film between the second driving roll and the second fixed roll becomes short, while moving the first moving roll such that the conveyance path of the electrolyte film between the first driving roll and the first fixed roll becomes long, with the first driving roll and the second driving roll stopped, in the processing. The region of the electrolyte film located between the first fixed roll and the second fixed roll is moved in the backward direction by moving the second moving roll such that the conveyance path of the electrolyte film between the second driving roll and the second fixed roll becomes short, while moving the first moving roll such that the conveyance path of the electrolyte film between the first driving roll and the first fixed roll becomes long. When the region of the electrolyte film located between the first fixed roll and the second fixed roll is moved in this manner in the backward direction, the image data as the reference for determining the correction value of the shading correction are acquired. Thus, after the image data as the reference for determining the correction value of the shading correction are acquired, the region of the electrolyte film whose image data as the reference for determining the correction value of the shading correction are acquired is located upstream of the part of the electrolyte film irradiated with light, in the forward direction. In consequence, the electrolyte film can also be inspected as to the region of the electrolyte film whose image data as the reference for determining the correction value of the shading correction are acquired.

Furthermore, the image data as the reference for determining the correction value of the shading correction may be acquired when the region of the electrolyte film located between the first fixed roll and the second fixed roll is moved in the forward direction, in the processing. The region of the electrolyte film located between the first fixed roll and the second fixed roll may be moved in the backward direction by moving the second moving roll such that the conveyance path of the electrolyte film between the second driving roll and the second fixed roll becomes short, while moving the first moving roll such that the conveyance path of the electrolyte film between the first driving roll and the first fixed roll becomes long, with the first driving roll and the second driving roll stopped, after the image data are acquired. When the region of the electrolyte film located between the first fixed roll and the second fixed roll is moved in the forward direction, the image data as the reference for determining the correction value of the shading correction are acquired. After the image data are acquired, the region of the electrolyte film located between the first fixed roll and the second fixed roll is moved in the backward direction by moving the second moving roll such that the conveyance path of the electrolyte film between the second driving roll and the second fixed roll becomes short, while moving the first moving roll such that the conveyance path of the electrolyte film between the first driving roll and the first fixed roll becomes long. Thus, the region of the electrolyte film whose image data as the reference for determining the correction value of the shading correction are acquired is located upstream of the part of the electrolyte film irradiated with light, in the forward direction. In consequence, the electrolyte film can also be inspected as to the region of the electrolyte film whose image data as the reference for determining the correction value of the shading correction are acquired.

According to the aspect of the present disclosure, even in the case where the process in which the electrolyte film cannot be conveyed in the backward direction is performed at a position upstream or downstream of the process of inspecting the film in the forward direction, the region of the electrolyte film whose image data as the reference for determining the correction value of the shading correction are acquired can be inspected.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein.

DETAILED DESCRIPTION OF EMBODIMENTS

First Embodiment

Figure 1:
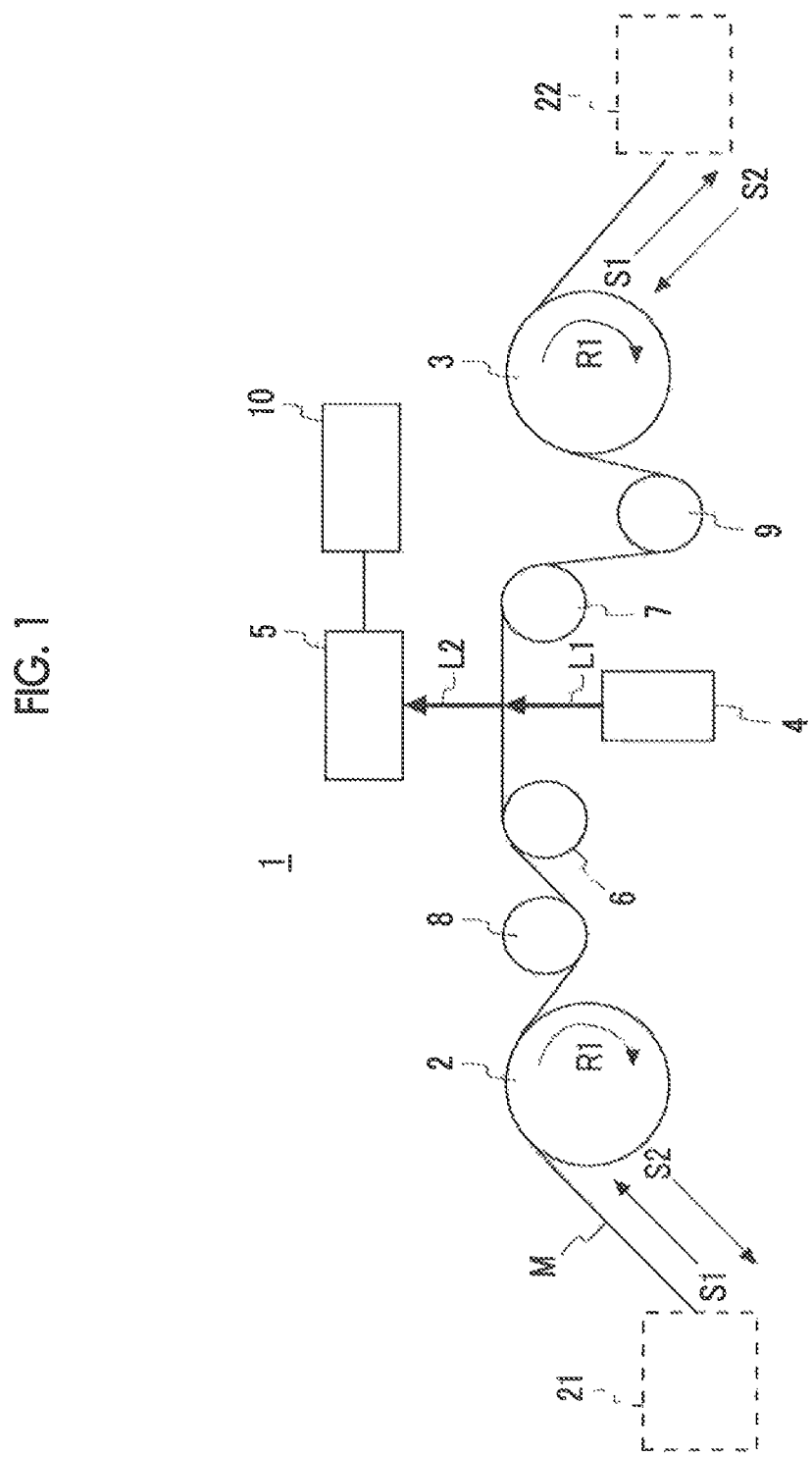
FIG. 1 is a view showing the general configuration of a film inspection device according to the first embodiment of the disclosure.

The first embodiment of the disclosure of the present disclosure will be described hereinafter with reference to the drawings. First of all, the general configuration of a film inspection device 1 according to the present embodiment of the disclosure will be described with reference to FIG. 1. The film inspection device 1 according to the present embodiment of the disclosure is used, for example, to inspect (a defect of) an electrolyte film such as a reinforced electrolyte film or the like for a polymer electrolyte fuel cell including a porous reinforcing member therein. FIG. 1 is a view showing the general configuration of the film inspection device 1 according to the present embodiment of the disclosure. As shown in FIG. 1, the film inspection device 1 is equipped with a first driving roll 2, a second driving roll 3, a light source 4, a camera 5, a first fixed roll 6, a second fixed roll 7, a first moving roll 8, and a second moving roll 9.

The first driving roll 2 and the second driving roll 3 stretch the electrolyte film M as an object for inspection from one surface side thereof. The first driving roll 2 and the second driving roll 3 are driven by a drive source such as a motor or the like. The light source 4 irradiates a part of the electrolyte film M located between the first driving roll 2 and the second driving roll 3 with the light L1. The light source 4 is, for example, a light emitting diode (an LED). The camera 5 is arranged facing the light source 4 across the electrolyte film M, and photographs (receives) light leaking from the electrolyte film M. The camera 5 is, for example, a line sensor camera that is constituted of fixed imaging elements (charge coupled devices or CCD's), a lens, a driver control circuit and the like. Incidentally, in the case where the camera 5 is a line sensor camera, the fixed imaging elements are arranged rectilinearly in a short-side direction (a width direction) of the electrolyte film M.

The first fixed roll 6 stretches the electrolyte film M from one surface side thereof between the part of the electrolyte film M irradiated with the light L and the first driving roll 2. The second fixed roll 7 stretches the electrolyte film from one surface side thereof between the part of the electrolyte film M irradiated with the light L1 and the second driving roll 3. The first moving roll 8 stretches the electrolyte film M from the other surface side thereof between the first driving roll 2 and the first fixed roll 6, and is movably configured. The second moving roll 9 stretches the electrolyte film M from the other surface side thereof between the second driving roll 3 and the second fixed roll 7, and is movably configured.

An upstream process 21 is a process that is performed at a position upstream of a process of inspecting the film by the film inspection device 1, in the forward direction S1. A downstream process 22 is a process that is performed at a position downstream of the process of inspecting the film by the film inspection device 1, in the forward direction S1. In the upstream process 21 and/or the downstream process 22, the electrolyte film M cannot be conveyed in the backward direction S2. It should be noted herein that the process in which the electrolyte film M cannot be conveyed in the backward direction S2 means a process in which some inconvenience is caused when the electrolyte film M is conveyed in the backward direction S2.

Next, the process in which the electrolyte film M cannot be conveyed in the backward direction will be concretely described citing, as an example, a process included in a method of manufacturing a reinforced electrolyte film. First of all, the outline of the method of manufacturing the reinforced electrolyte film will be described. The method of manufacturing the reinforced electrolyte film is equipped with a process of forming a bilaterally reinforced film having a band-shaped electrolyte polymer whose both surfaces are reinforced by a band-shaped reinforcing member, and a process of forming the reinforced electrolyte film by subjecting the bilaterally reinforced film to a hydrolysis treatment.

In the process of forming the bilaterally reinforced film, a first band-shaped reinforcing member that is supported by a back sheet is arranged on a surface of the band-shaped electrolyte polymer that is supported by a back sheet, and the band-shaped electrolyte polymer and the first band-shaped reinforcing member are thermally press-fitted to each other by a hot roller to form a unilaterally reinforced film. After that, the back sheet on the band-shaped electrolyte polymer side is peeled off from the unilaterally reinforced film. Then, a second band-shaped reinforcing member that is supported by a back sheet is arranged on a surface of the unilaterally reinforced film from which the back sheet on the band-shaped electrolyte polymer side has been peeled off, and the unilaterally reinforced film and the second band-shaped reinforcing member are thermally press-fitted to each other by the hot roller to form the bilaterally reinforced film. After that, the back sheet on the first band-shaped reinforcing member side is peeled off from the bilaterally reinforced film.

In the process of forming the reinforced electrolyte film by subjecting the bilaterally reinforced film to the hydrolysis treatment, the bilaterally reinforced film as an electrolyte precursor film is soaked in an alkali solution, and $-SO_2F$ groups as side-chain terminals belonging to the electrolyte polymer are denatured into $-SO_3Na$ groups. Then, the bilaterally reinforced film is washed with water and then soaked in an acid solution, so that the $-SO_3Na$ groups obtained through denaturation at the preceding stage are denatured into $-SO_3H$ groups. Thus, the reinforced electrolyte film is formed.

The aforementioned process of forming the bilaterally reinforced film is a process including a treatment of peeling off a base sheet from the electrolyte film, so the electrolyte film cannot be conveyed in the backward direction. This is because an inconvenience is caused in the electrolyte film if the base sheet peeled off from the electrolyte film M is stuck again on the electrolyte film by conveying the electrolyte film in the backward direction.

Besides, in the aforementioned process of forming the reinforced electrolyte film by subjecting the bilaterally reinforced film to the hydrolysis treatment, the electrolyte film cannot be conveyed in the backward direction. This is because an inconvenience is caused due to the fact that the alkali and acid solutions used for the hydrolysis treatment flow upward in the forward direction when the electrolyte film is conveyed in the backward direction.

Accordingly, the electrolyte film M cannot be conveyed in the backward direction in the process of forming the bilaterally reinforced film, and the process of forming the reinforced electrolyte film by subjecting the bilaterally reinforced film to the hydrolysis treatment, in the method of manufacturing the reinforced electrolyte film.

Next, the outline of a method of inspecting the electrolyte film M by the film inspection device 1 will be described. Incidentally, FIG. 1 will be referred to as appropriate in the following description. In inspecting the electrolyte film M, the first driving roll 2 and the second driving roll 3 are positively rotated (rotated in a direction indicated by the arrows R1 in FIG. 1), and the electrolyte film M is conveyed in the forward direction S1 from the first driving roll 2 toward the second driving roll 3. The light source 4 and the camera 5 are used to acquire image data for detecting a defect of the electrolyte film M. In concrete terms, while the electrolyte film M is conveyed as described above, one surface side of the electrolyte film M is irradiated with the light L1 from the light source 4, and the light L2 leaking from the other surface side of the electrolyte film M is continuously photographed through the use of the camera 5, so the image data for detecting the defect of the electrolyte film M are acquired. In the camera 5, the image data for detecting the defect of the electrolyte film M are constituted on an 8-bit gray scale (256 gradations). That is, in the camera 5, the intensity of light received by each pixel is converted into a numeral on the assumption that black and white correspond to 0 and 256 respectively.

The image data acquired by the camera 5 are transmitted to an analysis unit 10 of a computer or the like. In the analysis unit 10, the image data are subjected to processing procedures such as a filtering processing, a shading correction and the like. It should be noted herein that the filtering processing is designed for noise reduction and the like. The shading correction is designed to correct the dispersion of luminosity of light, the dispersion of texture of the electrolyte film M and the like that result from positional differences in the image photographed by the camera 5 with the electrolyte film M irradiated with the light L1 by the light source 4.

Incidentally, before the inspection of the electrolyte film M is started, a processing of acquiring image data as a reference for determining a correction value of the shading correction from the electrolyte film M as the object for inspection through the use of the light source 4 and the camera 5 needs to be performed. The details of the processing of acquiring the image data as the reference for determining the correction value of the shading correction from the electrolyte film M as the object for inspection will be described later.

After the image data for detecting the defect of the electrolyte film M are subjected to the shading correction, the filtering processing and the like, the analysis unit 10 determines whether or not each of the pixels in the image data is defective. The electrolyte film M and a defective region are different from each other in the amount of light received by the pixels. In the case where the defective region is a through-hole, the amount of light in the defective region is larger than the amount of light in the non-defective region. In the case where the defective region is a foreign matter, the amount of light in the defective region is smaller than the amount of light in the non-defective region. Accordingly, when the gradation value of a certain pixel in the image data for detecting the defect of the electrolyte film M is outside a range between an upper threshold (e.g., 200) and a lower threshold (e.g., 50), the analysis unit 10 determines that the pixel is defective. Then, the analysis unit 10 extracts a coordinate of the pixel recognized as a defect, and detect a position and shape of the defective region.

Figure 2:
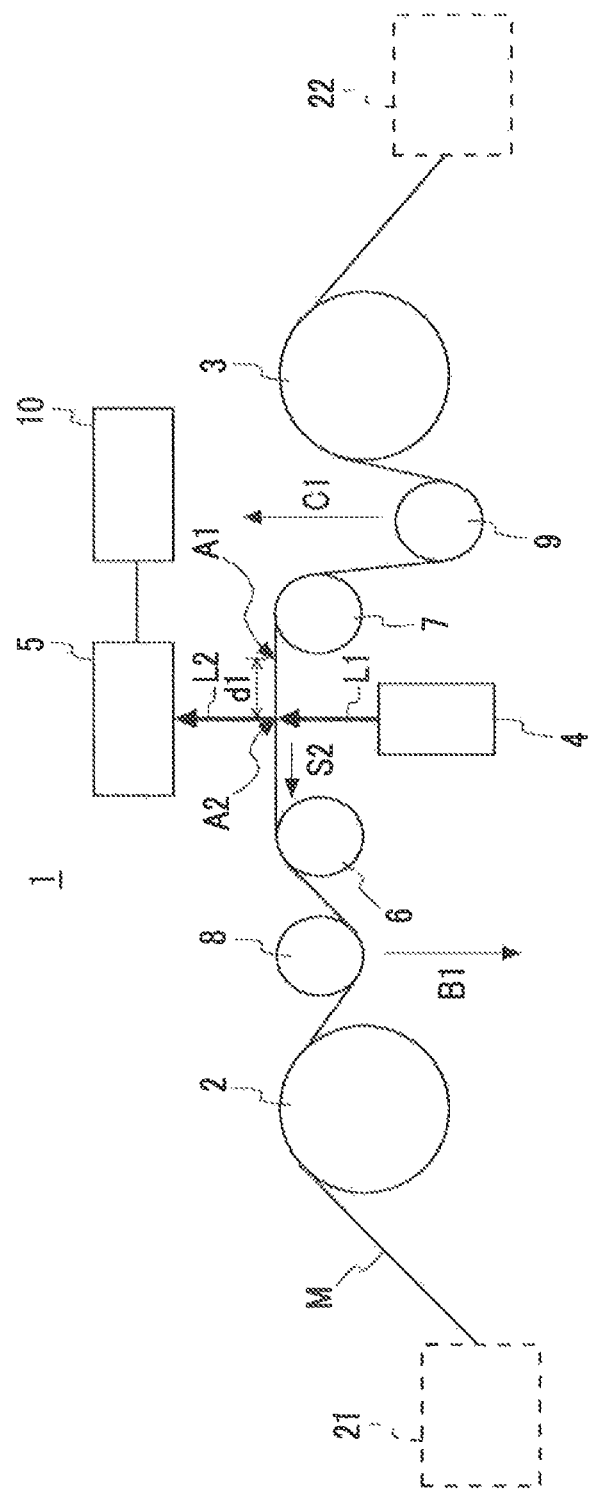
FIG. 2 is a view illustrating a processing of acquiring image data as a reference for determining a correction value of a shading correction from the electrolyte film M as an object for inspection, in the film inspection device according to the first embodiment of the disclosure.

Next, the processing of acquiring the image data as the reference for determining the correction value of the shading correction from the electrolyte film M as the object for inspection will be described. FIG. 2 is a view illustrating the processing of acquiring the image data as the reference for determining the correction value of the shading correction from the electrolyte film M as the object for inspection. As shown in FIG. 2, the second moving roll 9 is moved such that the conveyance path of the electrolyte film M between the second driving roll 3 and the second fixed roll 7 becomes short, while the first moving roll 8 is moved such that the conveyance path of the electrolyte film M between the first driving roll 2 and the first fixed roll 6 becomes long, with the first driving roll 2 and the second driving roll 3 stopped. That is, the second moving roll 9 is moved in a direction indicated by an arrow C1 in the drawing, while the first moving roll 8 is moved in a direction indicated by an arrow B1 in the drawing. Namely, the second moving roll 9 is moved in a first direction which intersects a direction in which the electrolyte film M is conveyed (in the first embodiment, the first direction is perpendicular to the direction in which the electrolyte film M is conveyed), while the first moving roll 8 is moved in a second direction which intersects the direction in which the electrolyte film M is conveyed (in the first embodiment, the second direction is completely opposite to the first direction).

By moving the first moving roll 8 and the second moving roll 9 in this manner, a part of the electrolyte film M located between the first fixed roll 6 and the second fixed roll 7 can be moved in the backward direction S2. For example, when the part located between the first fixed roll 6 and the second fixed roll 7 is moved in the backward direction S2 by a predetermined distance d1, the part of the electrolyte film M irradiated with the light L1 moves from a position A2 to a position A1.

When the first moving roll 8 and the second moving roll 9 are moved as described above to move the part of the electrolyte film M located between the first fixed roll 6 and the second fixed roll 7 in the backward direction S2, the image data as the reference for determining the correction value of the shading correction are acquired. For example, when the part located between the first fixed roll 6 and the second fixed roll 7 is moved in the backward direction S2 by the predetermined distance d1, the image data as the reference for determining the correction value of the shading correction are acquired by the camera 5 as to a region of the electrolyte film M located between the position A1 and the position A2.

Incidentally, in the aforementioned method of manufacturing the reinforced electrolyte film, in the case where the electrolyte film is inspected between the process of forming the bilaterally reinforced film and the process of forming the reinforced electrolyte film by subjecting the bilaterally reinforced film to the hydrolysis treatment, when the roll length of the electrolyte film as the object for inspection is 400 m, the predetermined distance d1 is 0.5 m.

Figure 3:
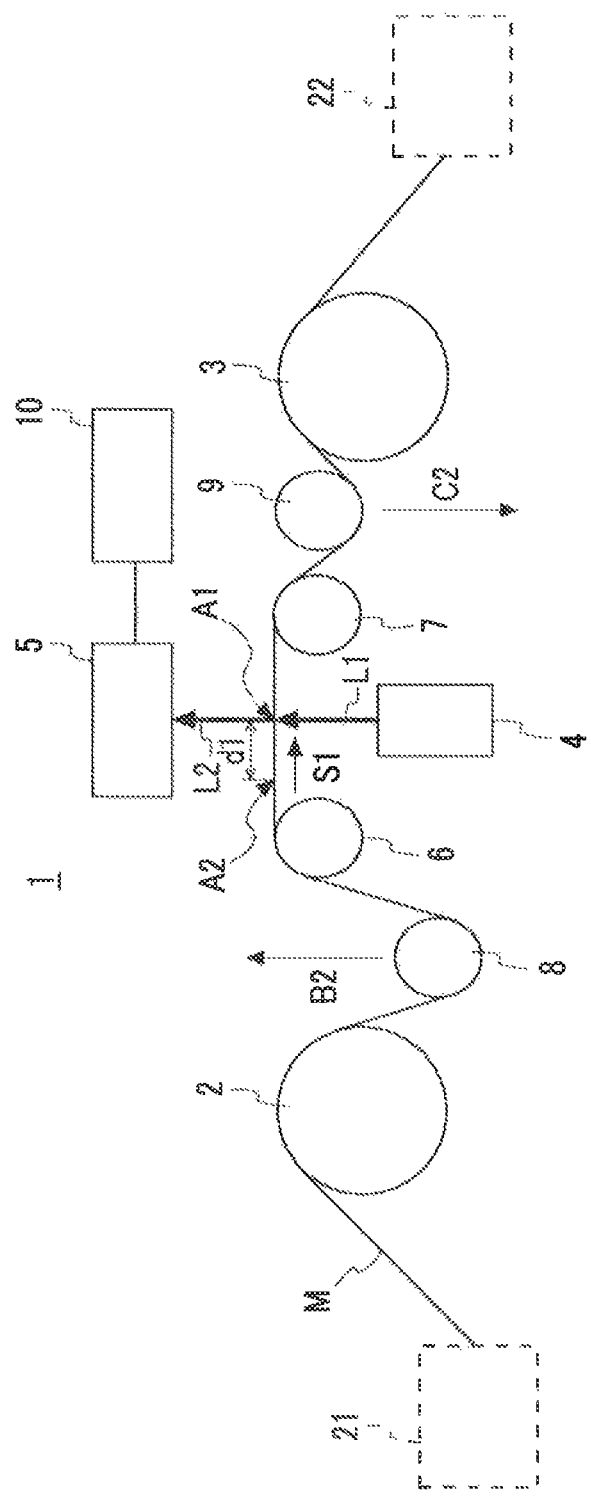
FIG. 3 is a view showing a view showing a state after the performance of the processing of acquiring the image data as the reference for determining the correction value of the shading correction, in the film inspection device according to the first embodiment of the disclosure.

FIG. 3 is a view showing a state after the performance of the processing of acquiring the image data as the reference for determining the correction value of the shading correction. As shown in FIG. 3, the electrolyte film M is irradiated with the light L1 at the position A1. The region of the electrolyte film M located between the position A1 and the position A2 is a region of the electrolyte film M whose image data as the reference for determining the correction value of the shading correction are acquired. That is, the region of the electrolyte film M whose image data as the reference for determining the correction value of the shading correction are acquired is located upstream of the part of the electrolyte film M irradiated with the light L1, in the forward direction S1.

The electrolyte film M is inspected while moving the electrolyte film M in the forward direction S1 by rotating the driving roll 2 and the driving roll 3 while the first moving roll 8 and the second moving roll 9 are not moved after the processing of acquiring the image data as the reference for determining the correction value of the shading correction. The region of the electrolyte film M whose image data as the reference for determining the correction value of the shading correction are acquired is located upstream of the part of the electrolyte film M irradiated with light, in the forward direction S1. Therefore, the electrolyte film M can also be inspected as to this region.

As another method, as shown in FIG. 3, after the performance of the processing of acquiring the image data as the reference for determining the correction value of the shading correction, the second moving roll 9 may be moved such that the conveyance path of the electrolyte film M between the second driving roll 3 and the second fixed roll 7 becomes long, while the first moving roll 8 is moved such that the conveyance path of the electrolyte film M between the first driving roll 2 and the first fixed roll 6 becomes short, with the first driving roll 2 and the second driving roll 3 stopped. That is, the second moving roll 9 may be moved in a direction indicated by an arrow C2 in the drawing while the first moving roll 8 is moved in a direction indicated by an arrow B2 in the drawing. Then, when the first moving roll 8 and the second moving roll 9 are moved to move the part of the electrolyte film M located between the first fixed roll 6 and the second fixed roll 7 in the forward direction S1, the electrolyte film M may be inspected.

Thus, the image data for detecting the defect of the electrolyte film M can be acquired as to the region of the electrolyte film M whose image data as the reference for determining the correction value of the shading correction are acquired (the region of the electrolyte film M located between the position A1 and the position A2), while the positions of the first moving roll 8 and the second moving roll 9 are returned to their original positions. It should be noted herein that the original positions mean positions before the performance of the processing of acquiring the image data as the reference for determining the correction value of the shading correction.

Incidentally, the electrolyte film M may be inspected when the first driving roll 2 and the second driving roll 3 are driven to move the part of the electrolyte film M located between the first fixed roll 6 and the second fixed roll 7 in the forward direction S1, after the performance of the processing of acquiring the image data as the reference for determining the correction value of the shading correction. In this case, the first moving roll 8 and the second moving roll 9 are returned to their original positions by moving the first moving roll 8 and the second moving roll 9 while rotating the first driving roll 2 and the second driving roll 3. Incidentally, in moving the first moving roll 8 and the second moving roll 9, the moving amount of the first moving roll 8 and the second moving roll 9 needs to be synchronized with the rotational speed of the first driving roll 2 and the second driving roll 3.

As described above, with the film inspection device 1 according to the present embodiment of the disclosure, in the case where the region of the electrolyte film M located between the first fixed roll 6 and the second fixed roll 7 is moved in the backward direction, which is the opposite of the forward direction, in the processing of acquiring the image data as the reference for determining the correction value of the shading correction, the second moving roll 9 is moved such that the conveyance path of the electrolyte film M between the second driving roll 3 and the second fixed roll 7 becomes short, while the first moving roll 8 is moved such that the conveyance path of the electrolyte film M between the first driving roll 2 and the first fixed roll 6 becomes long.

By moving the first moving roll 8 and the second moving roll 9 in this manner, the part of the electrolyte film M located between the first fixed roll 6 and the second fixed roll 7 can be moved in the backward direction S2, which is the opposite of the forward direction S1, without driving the second driving roll 3 to convey the electrolyte film in the backward direction. In consequence, the electrolyte film M can also be inspected as to the region of the electrolyte film M whose image data for determining the correction value of the shading correction are acquired. Thus, even in the case where the process in which the electrolyte film cannot be conveyed in the backward direction is performed at a position upstream or downstream of the process of inspecting the film in the forward direction, the region of the electrolyte film whose image data as the reference for determining the correction value of the shading correction are acquired can be inspected.

Second Embodiment

The second embodiment of the present disclosure will be described hereinafter with reference to the drawings. The film inspection device according to the present embodiment of the disclosure is identical in configuration to that described in the first embodiment of the disclosure through the use of FIG. 1. The present embodiment of the disclosure is different from the first embodiment of the disclosure only in the processing of acquiring the image data as the reference for determining the correction value of the shading correction from the electrolyte film M as the object for inspection.

In the film inspection device 1 according to the present embodiment of the disclosure, the processing of acquiring the image data as the reference for determining the correction value of the shading correction from the electrolyte film M as the object for inspection will be described. This processing includes an operation of acquiring the image data as the reference for determining the correction value of the shading correction from the electrolyte film M as the object for inspection, and an operation of returning the part of the electrolyte film M irradiated with the light L1 to its original position after the performance of the operation of acquiring the image data as the reference for determining the correction value of the shading correction. It should be noted herein that the original position means a position before the performance of the operation of acquiring the image data as the reference for determining the correction value of the shading correction from the electrolyte film M as the object for inspection.

Figure 4:
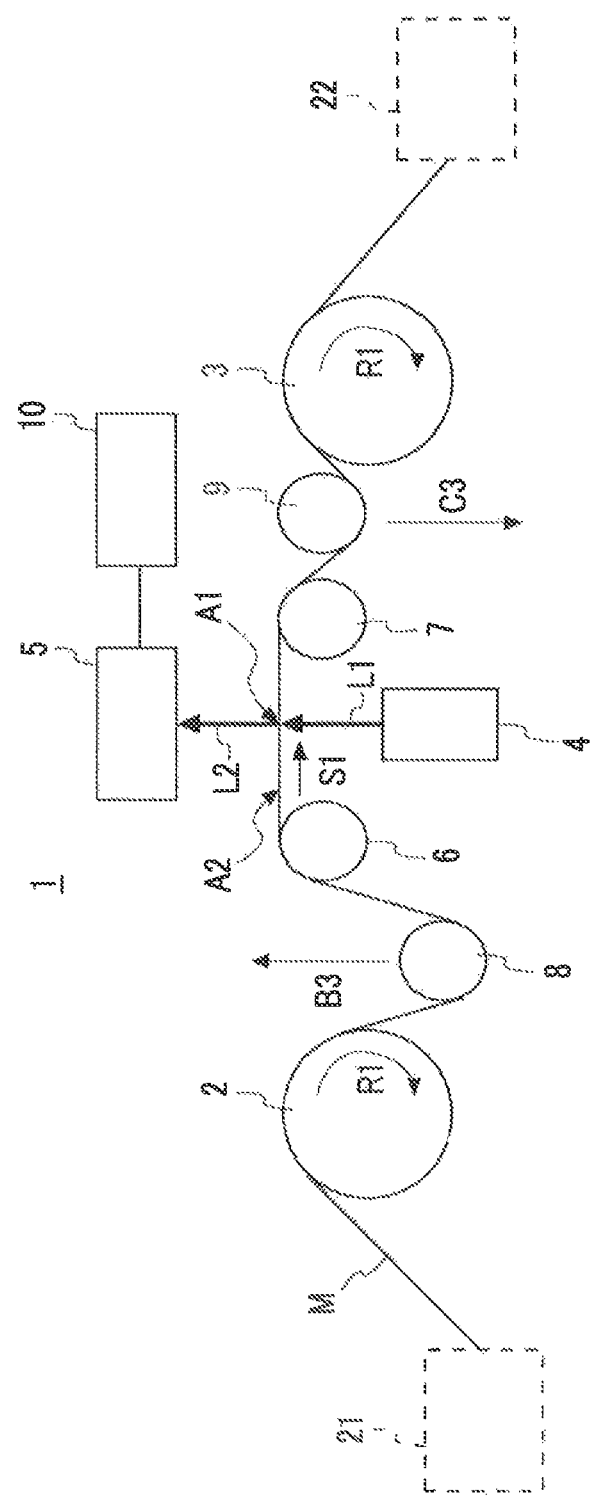
FIG. 4 is a view illustrating an operation of acquiring the image data as the reference for determining the correction value of the shading correction from the electrolyte film M as the object for inspection, in a film inspection device according to the second embodiment of the disclosure.

FIG. 4 is a view illustrating the operation of acquiring the image data as the reference for determining the correction value of the shading correction from the electrolyte film M as the object for inspection. As shown in FIG. 4, the second moving roll 9 is moved such that the conveyance path of the electrolyte film M between the second driving roll 3 and the second fixed roll 7 becomes long, while the first moving roll 8 is moved such that the conveyance path of the electrolyte film M between the first driving roll 2 and the first fixed roll 6 becomes short, with the first driving roll 2 and the second driving roll 3 stopped. That is, the second moving roll 9 is moved in a direction indicated by an arrow C3, while the first moving roll 8 is moved in a direction indicated by an arrow B3 in the drawing.

By moving the first moving roll 8 and the second moving roll 9 in this manner, the part of the electrolyte film M located between the first fixed roll 6 and the second fixed roll 7 can be moved in the forward direction S1 by the predetermined distance d1. Thus, the part of the electrolyte film M irradiated with the light L1 moves from the position A1 to the position A2, and the image data as the reference for determining the correction value of the shading correction are acquired by the camera 5 as to the region of the electrolyte film M located between the position A1 and the position A2.

Figure 5:
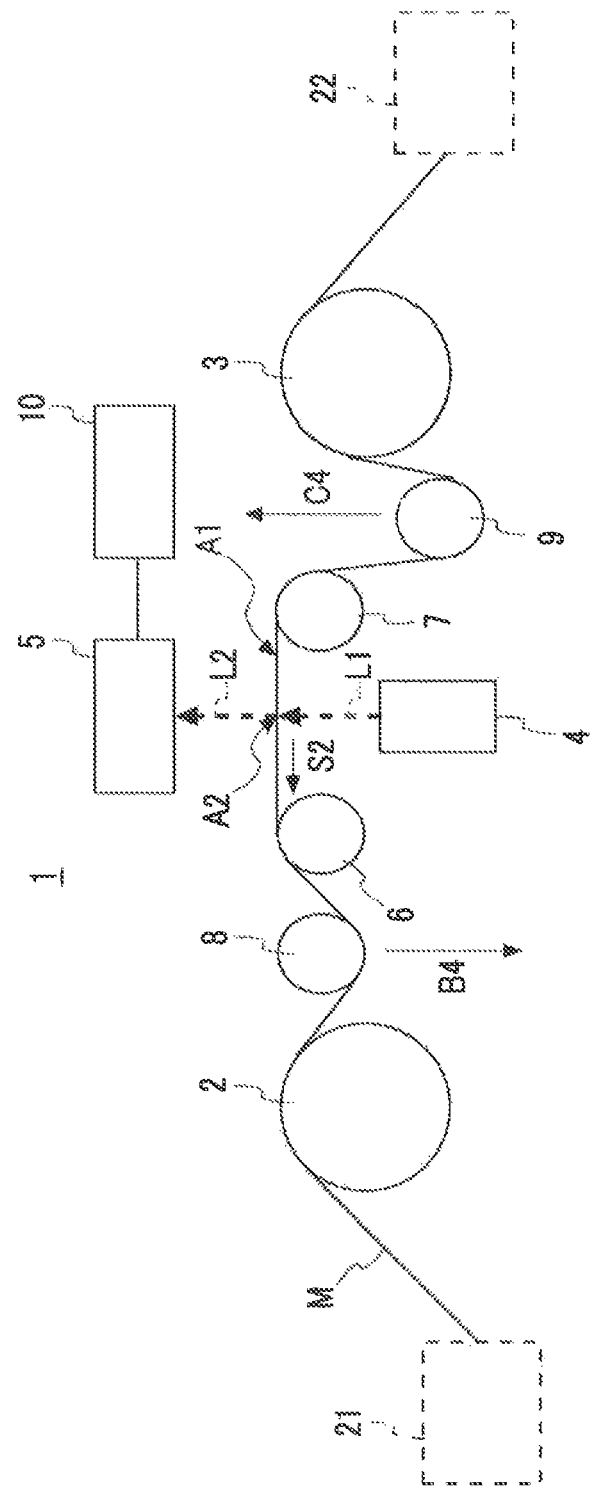
FIG. 5 is a view illustrating an operation of returning a part of the electrolyte film irradiated with light to its original position after the performance of the operation of acquiring the image data as the reference for determining the correction value of the shading correction, in the film inspection device according to the second embodiment of the disclosure.
Figure 6:
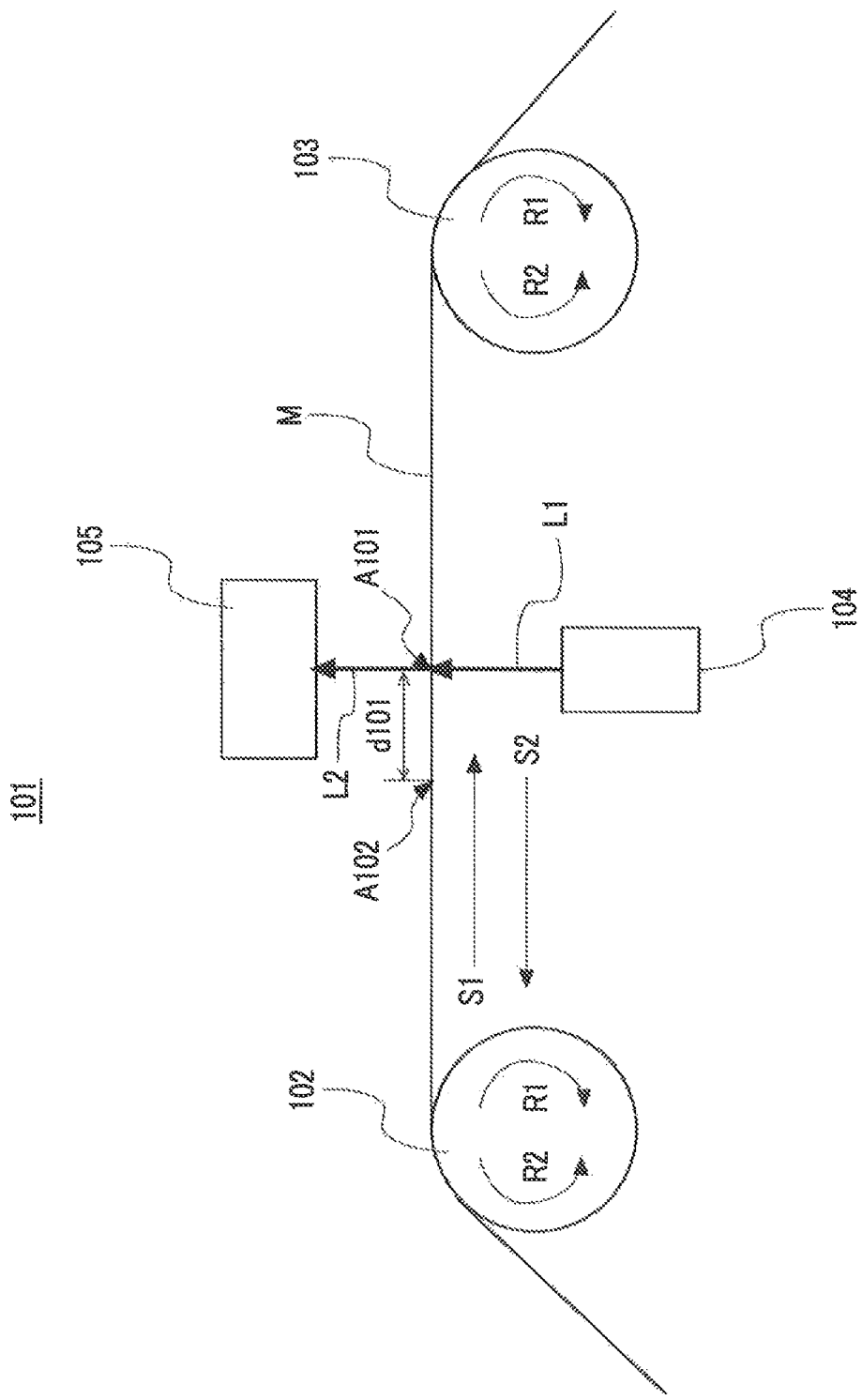
FIG. 6 is a schematic view showing the general configuration of the existing film inspection device.

FIG. 5 is a view illustrating the operation of returning the part of the electrolyte film M irradiated with the light L1 to its original position after acquiring the image data as the reference for determining the correction value of the shading correction. As shown in FIG. 5, the second moving roll 9 is moved such that the conveyance path of the electrolyte film M between the second driving roll 3 and the second fixed roll 7 becomes short, while the first moving roll 8 is moved such that the conveyance path of the electrolyte film M between the first driving roll 2 and the first fixed roll 6 becomes long, with the first driving roll 2 and the second driving roll 3 stopped. That is, the second moving roll 9 is moved in a direction indicated by an arrow C4 while the first moving roll 8 is moved in a direction indicated by an arrow B4 in the drawing.

When the first moving roll 8 and the second moving roll 9 are moved in this manner, the part of the electrolyte film M located between the first fixed roll 6 and the second fixed roll 7 can be moved in the backward direction S2. When the part of the electrolyte film M located between the first fixed roll 6 and the second fixed roll 7 is moved by the predetermined distance d1, the part of the electrolyte film M irradiated with the light L1 moves from the position A2 to the position A1. That is, the part of the electrolyte film M irradiated with the light L1 can be returned to its original position. Besides, the positions of the first moving roll 8 and the second moving roll 9 can also be returned to their positions prior to the acquisition of the image data as the reference for determining the correction value of the shading correction.

Incidentally, in the operation of acquiring the image data as the reference for determining the correction value of the shading correction from the electrolyte film M as the object for inspection, the part of the electrolyte film M located between the first fixed roll 6 and the second fixed roll 7 may be moved in the forward direction S1 by driving the first driving roll 2 and the second driving roll 3.

As described above, the film inspection device 1 according to the present embodiment of the disclosure acquires the image data as the reference for determining the correction value of the shading correction when the region of the electrolyte film M located between the first fixed roll 6 and the second fixed roll 7 is moved in the forward direction S1. After that, the region of the electrolyte film M located between the first fixed roll 6 and the second fixed roll 7 is moved in the backward direction S2, which is the opposite of the forward direction S1, by moving the second moving roll 9 such that the conveyance path of the electrolyte film M between the second driving roll 3 and the second fixed roll 7 becomes short, while moving the first moving roll 8 such that the conveyance path of the electrolyte film M between the first driving roll 2 and the first fixed roll 6 becomes long.

Thus, the region of the electrolyte film M whose image data as the reference for determining the correction value of the shading correction are acquired is located upstream of the part of the electrolyte film M irradiated with light, in the forward direction S1. In consequence, the electrolyte film M can also be inspected as to the region of the electrolyte film M whose image data as the reference for determining the correction value of the shading correction are acquired.

Incidentally, the present disclosure is not limited to the aforementioned embodiments of the disclosure, but can be appropriately changed within such a range as not to depart from the gist thereof.

What is claimed is:

1. A film inspection device comprising:
a first driving roll that stretches an electrolyte film as an object for inspection from one surface side of the electrolyte film;
a second driving roll that stretches the electrolyte film as the object for inspection from the one surface side of the electrolyte film;
a light source that irradiates a part of the electrolyte film located between the first driving roll and the second driving roll with light;
a camera that is arranged facing the light source across the electrolyte film and that photographs light leaking from the electrolyte film;
a first fixed roll that stretches the electrolyte film from the one surface side of the electrolyte film between the part of the electrolyte film irradiated with light and the first driving roll;
a second fixed roll that stretches the electrolyte film from the one surface side of the electrolyte film between the part of the electrolyte film irradiated with light and the second driving roll;
a first moving roll that stretches the electrolyte film from the other surface side of the electrolyte film between the first driving roll and the first fixed roll and that is movably configured; and
a second moving roll that stretches the electrolyte film from the other surface side of the electrolyte film between the second driving roll and the second fixed roll and that is movably configured, wherein
the second moving roll is moved such that a conveyance path of the electrolyte film between the second driving roll and the second fixed roll becomes short, while the first moving roll is moved such that the conveyance path of the electrolyte film between the first driving roll and the first fixed roll becomes long with the first driving roll and the second driving roll stopped, in a case where a region of the electrolyte film located between the first fixed roll and the second fixed roll is moved in a backward direction, which is an opposite of a forward direction from the first driving roll toward the second driving roll, in a processing of acquiring image data as a reference for determining a correction value of a shading correction, and
the electrolyte film is inspected while being conveyed in the forward direction.

2. The film inspection device according to claim 1, wherein
the image data as the reference for determining the correction value of the shading correction are acquired when the region of the electrolyte film located between the first fixed roll and the second fixed roll is moved in the backward direction by moving the second moving roll such that the conveyance path of the electrolyte film between the second driving roll and the second fixed roll becomes short, while moving the first moving roll such that the conveyance path of the electrolyte film between the first driving roll and the first fixed roll becomes long, with the first driving roll and the second driving roll stopped, in the processing.

3. The film inspection device according to claim 1, wherein
the image data as the reference for determining the correction value of the shading correction are acquired when the region of the electrolyte film located between the first fixed roll and the second fixed roll is moved in the forward direction, in the processing, and
the region of the electrolyte film located between the first fixed roll and the second fixed roll is moved in the backward direction by moving the second moving roll such that the conveyance path of the electrolyte film between the second driving roll and the second fixed roll becomes short, while moving the first moving roll such that the conveyance path of the electrolyte film between the first driving roll and the first fixed roll becomes long, with the first driving roll and the second driving roll stopped, after the image data are acquired.

\* \* \* \* \*